US012697143B2

(12) United States Patent

Hu

(10) Patent No.: US 12,697,143 B2

(45) Date of Patent: Aug. 4, 2026

(54) MULTIFUNCTIONAL TRACTION AND BONE FIXATION DEVICE

(71) Applicant: Chengji Hu, Yueqing City (CN)

(72) Inventor: Chengji Hu, Yueqing City (CN)

( * ) Notice: Subject to any disclaimer, the term of this patent is extended or adjusted under 35 U.S.C. 154(b) by 918 days.

(21) Appl. No.: 17/993,971

(22) Filed: Nov. 24, 2022

(65) Prior Publication Data

US 2023/0087591 A1 Mar. 23, 2023

Related U.S. Application Data

(63) Continuation-in-part of application No. PCT/CN2021/000106, filed on May 14, 2021.

(30) Foreign Application Priority Data

May 25, 2020 (CN) .......................... 202010465683.3

(51) Int. Cl.
A61B 17/66 (2006.01)
A61B 17/64 (2006.01)
A61B 17/60 (2006.01)

(52) U.S. Cl.
CPC .......... A61B 17/66 (2013.01); A61B 17/6441 (2013.01); A61B 17/6458 (2013.01); *A61B 2017/606* (2013.01)

(58) Field of Classification Search
CPC ... A61B 17/58; A61B 17/6491; A61B 17/645; A61B 17/64; A61B 17/6408; A61B 17/60; A61B 17/6458; A61B 17/6441; A61B 17/66; A61B 2017/603–606
See application file for complete search history.

(56) References Cited

U.S. PATENT DOCUMENTS 2,024,325 A * 12/1935 Allen ................. A61B 17/6408
606/56
2,079,567 A * 5/1937 Anderson ................. A61F 5/04
602/39
4,360,012 A * 11/1982 McHarrie .......... A61B 17/6441
606/54

(Continued)

FOREIGN PATENT DOCUMENTS

CN 201275128 Y 7/2009
CN 202136454 U 2/2012

(Continued)

OTHER PUBLICATIONS

International search report of PCT/CN2021/000106.

*Primary Examiner* — Eduardo C Robert
*Assistant Examiner* — Michelle C Green

(57) ABSTRACT

A multifunctional traction and bone fixation device relates to the technical field of medical devices. Two traction clamping plates serve as a base. The front of each of the two traction clamping plates defines a traction nail. The middle portion of the clamping plate is arranged with a positioning and pressurizing screw. The rear end of the clamp plate is arranged with a traction handle screw. The clamping plate is arranged with a plurality of auxiliary fixation pin holders and auxiliary fixation pins. Heads of two traction nails are injected in opposite directions into a lower portion of a fracture site to determine a fixation position. Rear ends of the two traction clamping plates extend along the thigh direction to be weighted-pulled.

10 Claims, 12 Drawing Sheets

(56) References Cited

U.S. PATENT DOCUMENTS

2003/0055425 A1 *  3/2003  Hajianpour ............ A61B 17/60
                                                    606/57
2010/0076434 A1 *  3/2010  Hajianpour ............ A61B 17/66
                                                    606/54
2017/0189068 A1 *  7/2017  Fisher .................. A61B 17/645

FOREIGN PATENT DOCUMENTS

CN        202335915  U      7/2012
CN        103445831  A     12/2013
CN        208677476  U      4/2019
GB          2425958  A  * 11/2006   ......... A61B 17/6458
WO       2006126033  A1    11/2006

* cited by examiner

MULTIFUNCTIONAL TRACTION AND BONE FIXATION DEVICE

CROSS REFERENCE TO RELATED APPLICATIONS

The present application is a continuation-application of International (PCT) Patent Application No. PCT/CN2021/000106, filed on May 14, 2021, which claims the priority of the Chinese patent application No. 202010465683.3, filed on May 25, 2020, and the entire contents of which are hereby incorporated by reference in their entireties.

TECHNICAL FIELD

The present disclosure relates to the field of multifunctional traction and bone fixation devices for medical surgeries, and the traction and bone fixation device is mainly used for minimally invasive treatment and is configured to tract and fix fractured or comminuted fractured human limbs.

BACKGROUND

At present, there are various methods to treat fractured human limbs in the medical field. In Chinese medicine, conservative treatments may be performed as follows: 1, taking a plaster to fix the fractured limbs externally; and 2, taking clamping plates to fix the fractured limbs externally. These treatments may only be useful for minor injuries where bones are cracked, but a completely displaced fractured bone cannot be accurately positioned. In western medicine, a traditional traction treatment may be applied, where a traction nail is injected into the human body and penetrates the bones. Advantages of the western treatment may be small scars being generated. Disadvantages of the western treatment may include the following. 1. The traditional traction nail is configured as a single nail. In order to inject the traction nail into the human body, the traction nail has to penetrate the bone, generating massive vibration. The vibration may cause the fractured bone to be completely displaced, resulting in secondary injuries. 2. The traditional traction nail may penetrate one bone only after being injected into the human body. However, a lower limb of the human includes two bones, and therefore, the traditional traction nail may not be applicable appropriately. Therefore, the doctor may inject the traction nail into a heel bone. Since the heel bone and two calf bones do not extend in a vertical line, a traction effect may not be guaranteed. Therefore, when the western treated is performed in hospital, an open surgery may be performed, taking a steel plate to fix the bones internally. Internal fixation with the plate seems applicable, but is a less scientific treatment and may cause damage. 1. Patients may fear psychologically about the open surgery. 2. Lumbar anesthesia may make the patient to feel bad. Some patients may have bruising and have lumbar joint injury due to improper anesthesia. Since blood circulation may be poor at the lumbar joint, the lumbar may be swelling for a long period of time, and sequelae may be caused. 3. When the open surgery is performed and steel-plate fixation is performed, a shape and a configuration of the plate may not exactly match a natural shape of the bone. In addition, the doctor may perform the open surgery while the patient is bleeding. Therefore, the doctor may have poor vision from three viewing sides when joining the bones in a small operation window. After the surgery, abnormal alignment and failure in meeting anatomical alignment requirements may occur, which may cause the bone to grow slowly, and a secondary surgery may be required. In some cases, a bone may be implanted (taking the above to fix the bottom). Further, the inaccurate alignment and a serious alignment error may cause patients to have lifelong disability. 4. Even when the surgery goes well, a year later, the internal fixation needs to be removed by performing another surgery, which may bring a secondary injury. When removing the internal fixation, the vision may be blurred, and a location of the fixation may not be easily found, increasing damages to the human body caused by the surgical. A retractable traction arch is available in the art, replacing a traditional traction rope. A screw-in traction arch is also available in the art and injects traction nails into two sides of the ankle. A design concept of the screw-in traction arch may be good, but a mechanical principle of the screw-in traction arch is not well designed. An upper end of the traction arch has two screw holes, and screws may be screwed into the screw holes for fixation. The screw-in traction arch may have the following disadvantages. 1. Rotating a screw into a screw pattern may strangle epidermis of muscles and bones. 2. A head of the screw that is screwed into the hole abuts against the bone cortex, and a traction weight is arranged to increase the tension, such that the patient may feel the pain and may not sleep well, and the screw may slip when the patient is turning his body, tearing the muscle. 3. When a screwing force is increased, the muscle, which is strangled due to rotating the screw, may be brought into the bone to cause infection. Therefore, the traction arch in the art is not configured properly, and no other treatment functions may be achieved.

SUMMARY OF THE DISCLOSURE

In order to solve the above technical problems, the present disclosure provides a multifunctional traction and bone fixation device. By using the multifunctional traction and bone fixation device, the doctor may select suitable components to assemble the traction fixation device in advance based on displacement of fractured bones of the patient. Generally, the open surgery may not be performed unless the bones are seriously comminutedly fractured. The doctor may directly inject traction nails into two sides of a lower portion of a fracture, such that a fixation position may be determined, and a traction treatment may be performed. When the plantar heel and a bone near a joint is fractured, or when fractures are located at a plurality of positions, an auxiliary fixation may be needed, traction may be performed, and then a corresponding auxiliary fixation assembly may be assembled. The multifunctional traction and bone fixation device may be assembled easily, and positioning may be adjustable and stable. The patient may not suffer from a plurality of surgeries. Therefore, the multifunctional traction and bone fixation device may be the new treatment technique of traction and fixation in the minimally invasive medical field.

According to the multifunctional traction and bone fixation device provided by the present disclosure, reasonable treatments are provided for various types of bone fractures. The applicant has performed extensive research of many years to successfully develop a set of components that are assembled in various ways. The assembling matches with displacement of fractured bones to meet requirements of a wider and better traction and fixation, and the assembled device may be easily operated. Detailed configuration of the device may be as follows. The multifunctional traction and bone fixation device includes two traction clamping plates. A front end of each of the two traction clamping plates is arranged with a traction nail. A middle portion of each of the two traction clamping plates is arranged with a positioning and pressurizing screw. A rear end of each of the two traction clamping plates is arranged with a traction handle screw. By configuring the positioning and pressurizing screw at the middle portion of the traction clamping plate and the traction handle screw at the rear end of the traction clamping plate, a framework of the traction device is formed. A plurality of auxiliary fixation pin holders are arranged on the middle portion of the traction clamping plate and the positioning and pressurizing screw. The plurality of auxiliary fixation pin holders include an integral auxiliary fixation pin holder and a split auxiliary fixation pin holder. Each auxiliary fixation pin holder is arranged with an auxiliary fixation pin. A top of each of the two traction clamping plates is arranged with a nail protection screw.

The multifunctional traction and bone fixation device includes two traction clamping plates, serving as a base. The front of each of the two traction clamping plates defines a plurality of traction nail mounting holes. The user may determine which mounting hole is to be taken for assembling the device. After traction nails are mounted into the mounting holes, a reinforcement nut may be arranged for adjustment and fixation. Further, a nail protection sleeve structure may be included. Welding or conjoining may be performed to form a two-phase "pincer hook". The middle portion of the clamping plate defines a plurality of mounting holes. The user may determine which mounting hole is to be taken for assembling the device. After the positioning and pressurizing screws are mounted into the mounting holes, reinforcement nuts are arranged for adjustment and fixation. The rear end of the clamp plate defines mounting holes. After traction handle screws are mounted into the mounting holes, reinforcement nuts are arranged for adjustment and fixation. The middle portion of the clamping plate defines a plurality of screw holes, and the auxiliary fixation pin holders are mounted in the plurality of screw holes. The auxiliary fixation pin holders include the following two types. The auxiliary fixation pin holders include the integral auxiliary fixation pin holder and the split auxiliary fixation pin holder. The integral fixation pin holder is arranged on a body of the traction clamping plate. The split fixation pin holder is fixedly arranged by a screw. Each auxiliary fixation pin holder is arranged with an auxiliary fixation pin, and the reinforcement nut is arranged for adjustment and fixation. A middle portion of the positioning and pressurizing screw may be round or squared. The squared middle portion of the positioning and pressurizing screw may provide a base for the auxiliary fixation, allowing the assembling to be achieved easily. The squared middle portion of the positioning and pressurizing screw may be configured to increase fixation when being applied for the heel bone and fractures occurred at middle joint parts. The top of the traction clamping plate is arranged with screw holes for arranging screw protection nuts, protecting an angle of the traction nail, preventing a nail head from slipping out. The nail being screwed in and out may be adjusted. A spring and a flat pad are arranged may be an innovation in external fixation medicine. The spring may function as a robot hand to push the fixed pin, and a natural pressurizing and fixation effect may be achieved.

4

Figure 2:
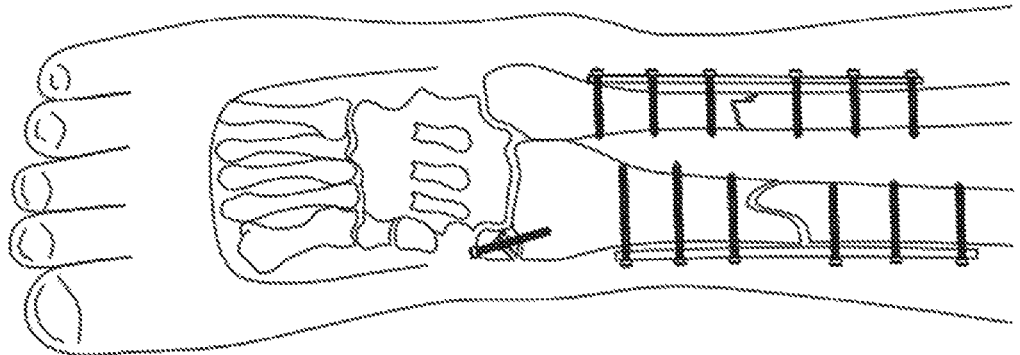

FIG. 2 is a plane schematic view of taking steel plates and screws for internally fixation when preforming a traditional open surgery to treat fractures of a lower leg.

Figure 3:
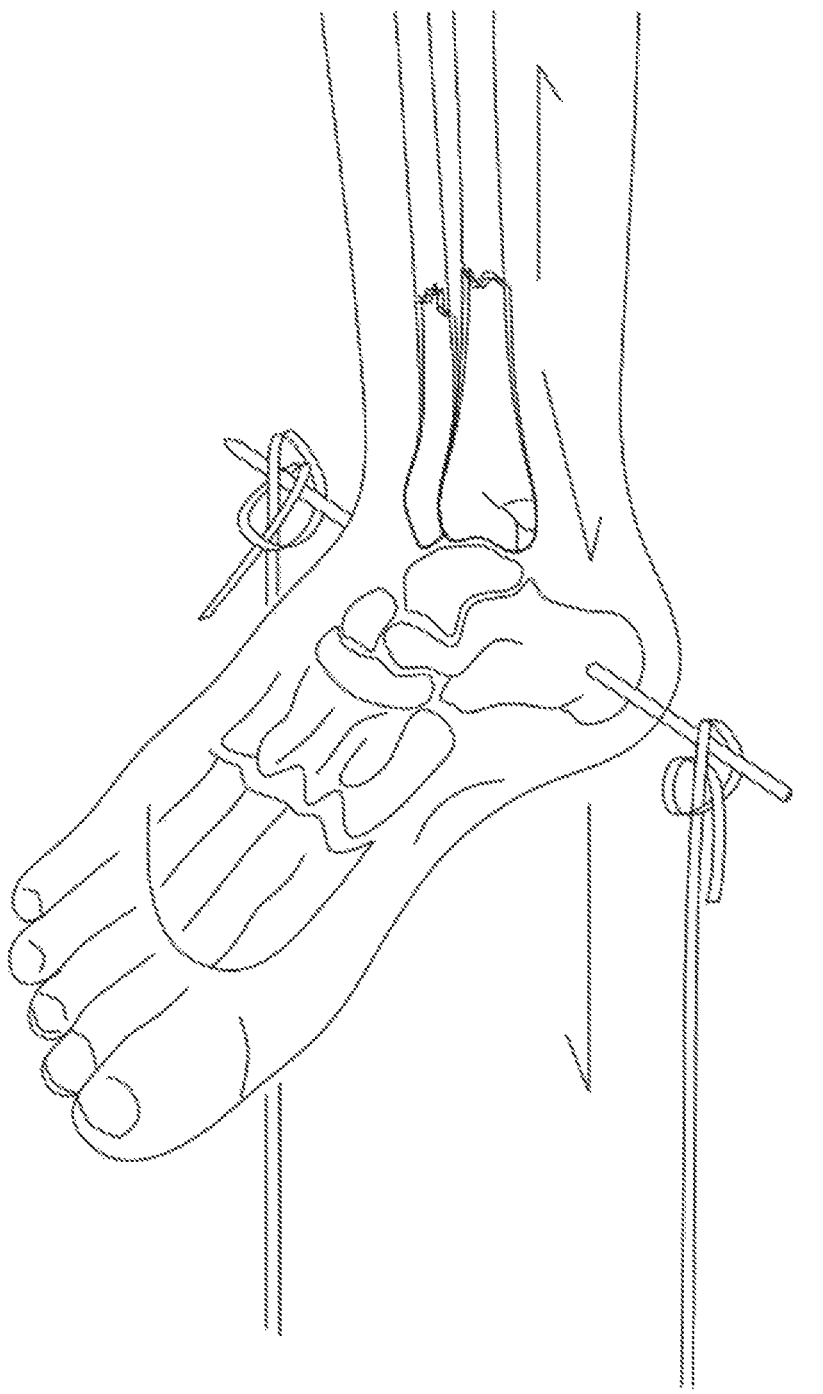

FIG. 3 is a schematic view of opposite positions of a fracture site in which the traction nail is injected, when traditional traction is performed to treat fractures of a lower leg.

Figure 4:
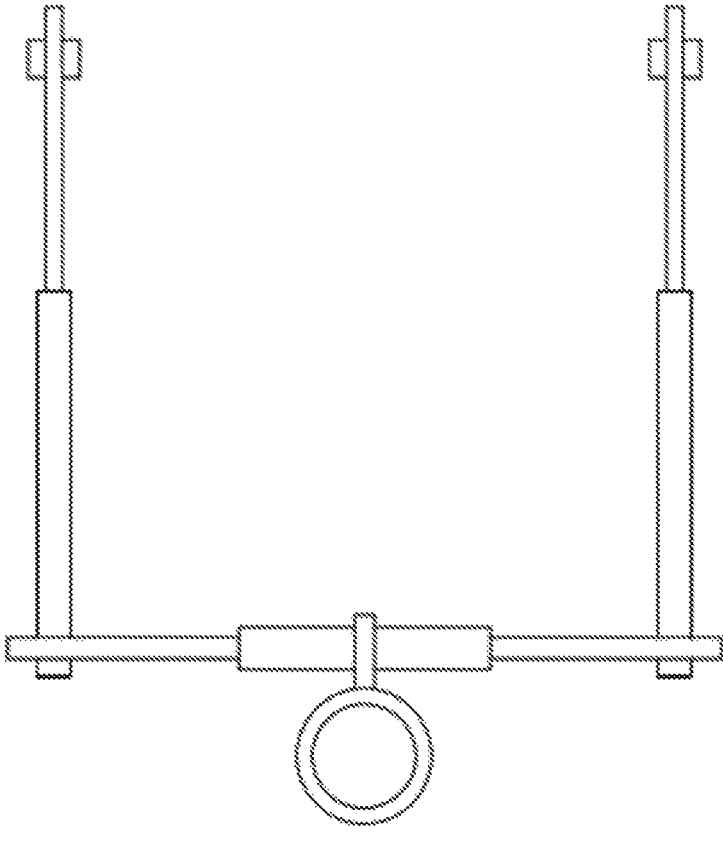

FIG. 4 is a retractable traction arch.

Figure 5:
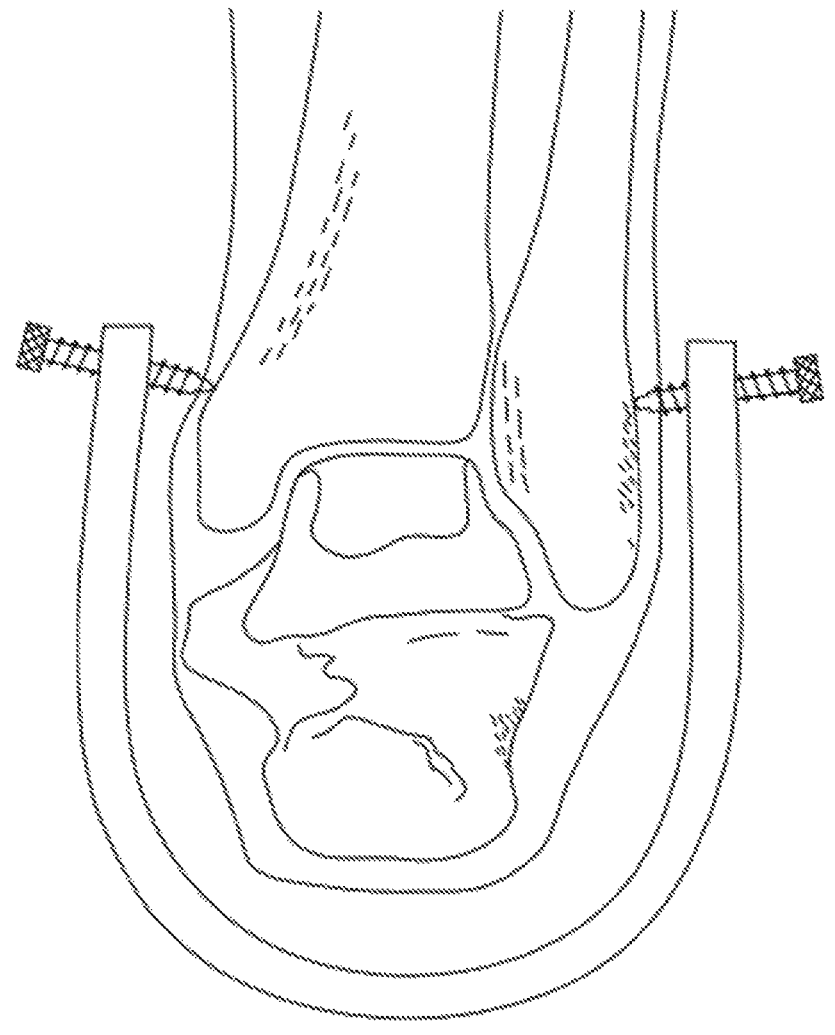

FIG. 5 is a screw-in traction arch.

Figure 6:
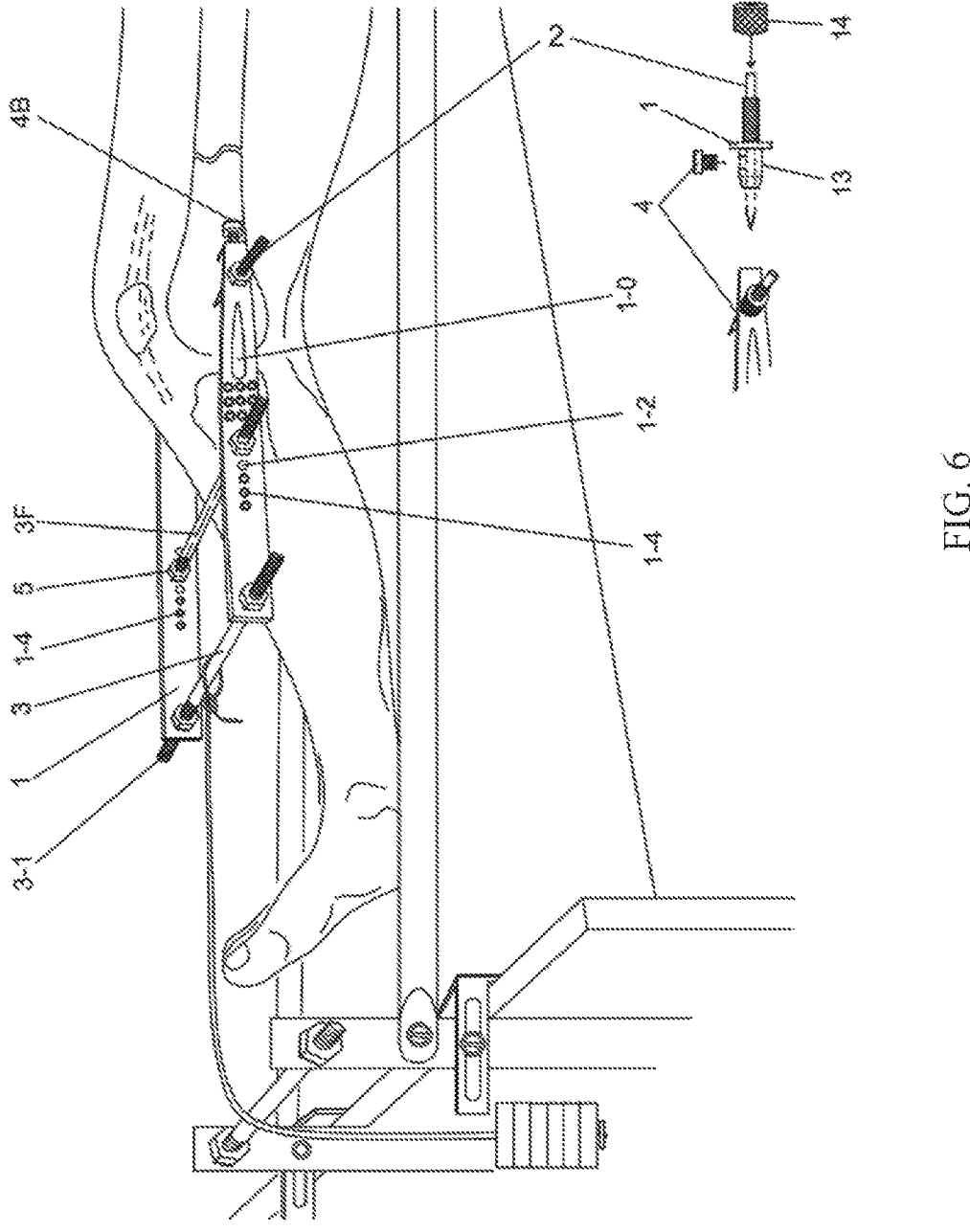

FIG. 6 is a side schematic view of taking a multifunctional traction and bone fixation device to perform traction treatment to treat the fractured dice bone according to an embodiment of the present disclosure.

Figure 7:
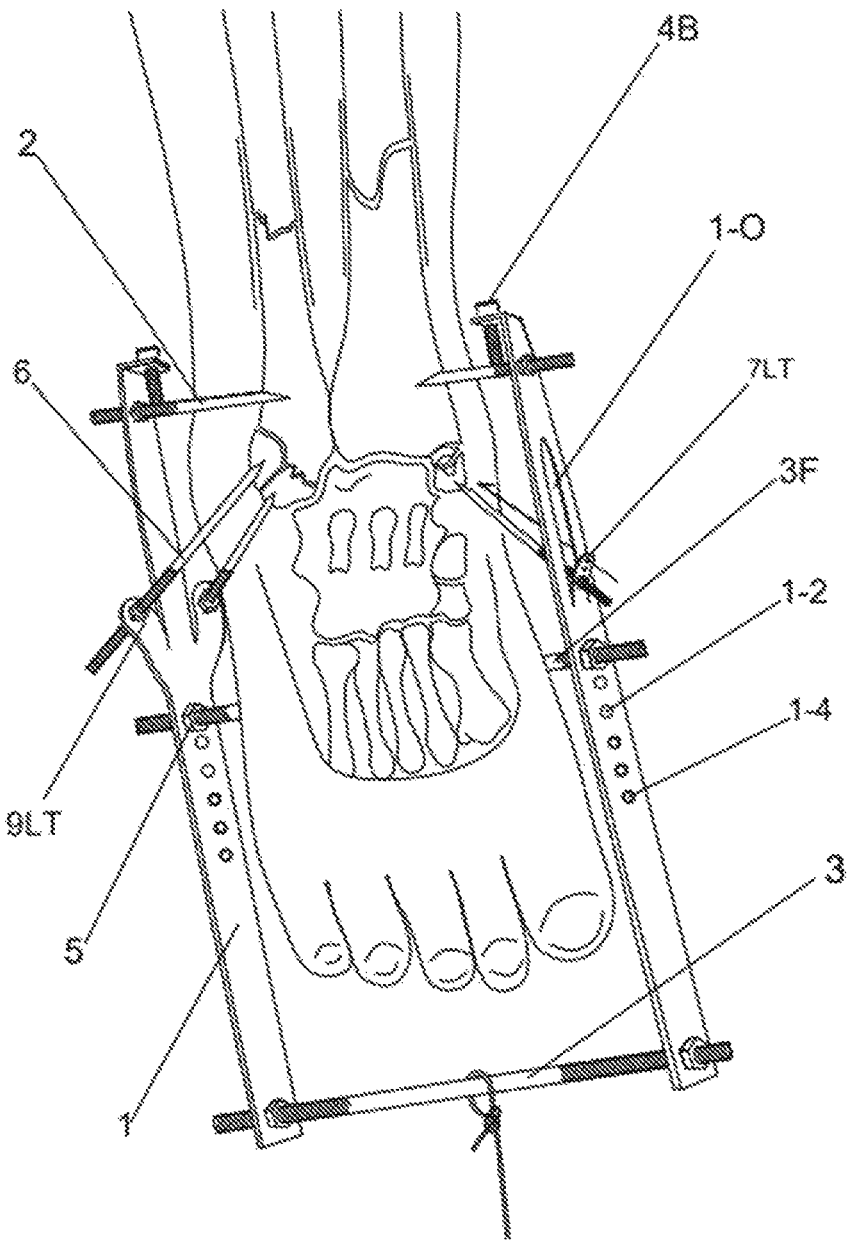

FIG. 7 is a plane view of taking the multifunctional traction and bone fixation device to perform traction and auxiliary fixation treatment to treat the lower leg having various fractures according to an embodiment of the present disclosure.

Figure 8:
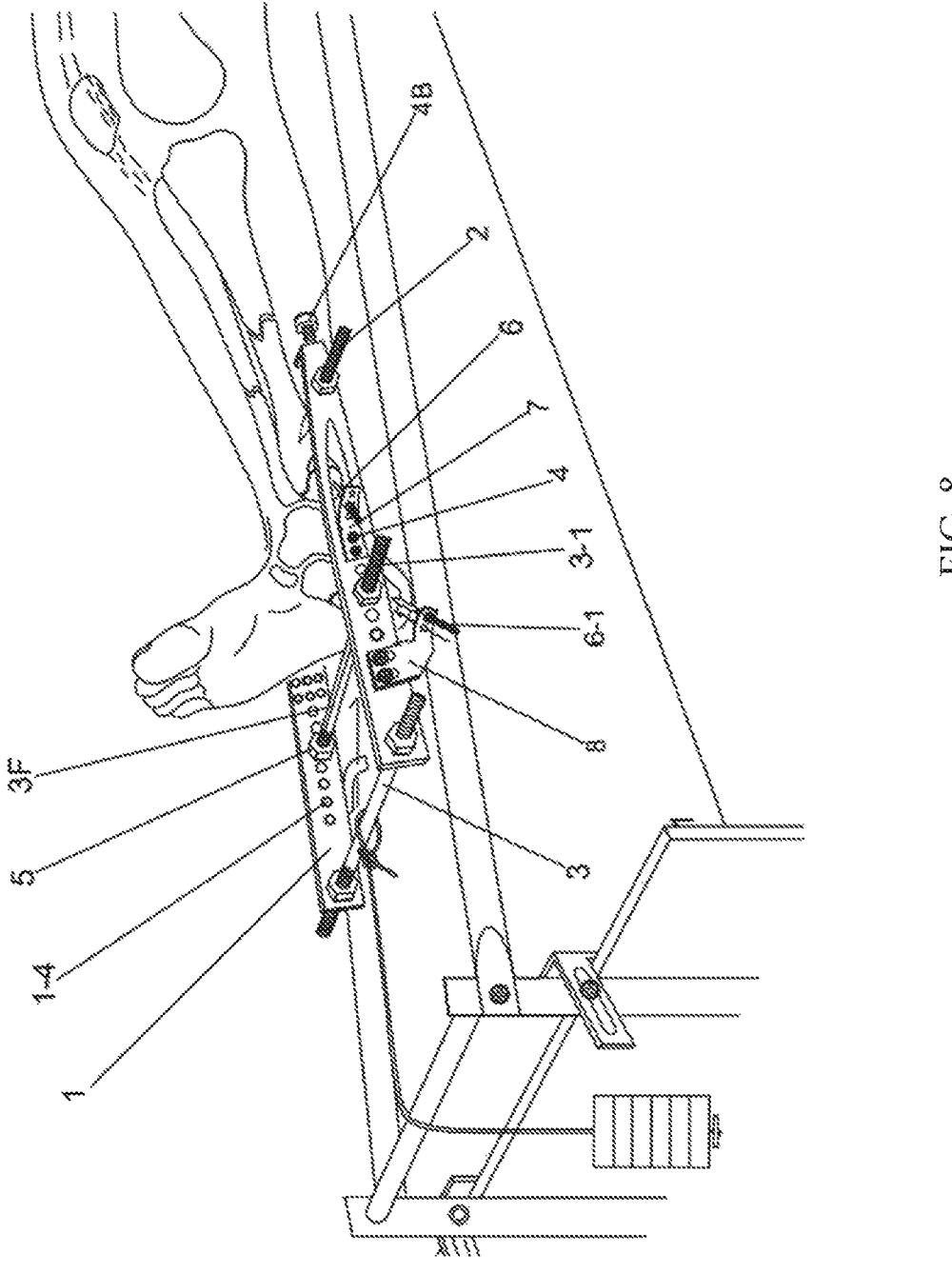

FIG. 8 is a side view of taking the multifunctional traction and bone fixation device to perform traction and auxiliary fixation treatment to treat the lower leg having various fractures according to an embodiment of the present disclosure.

Figure 9:
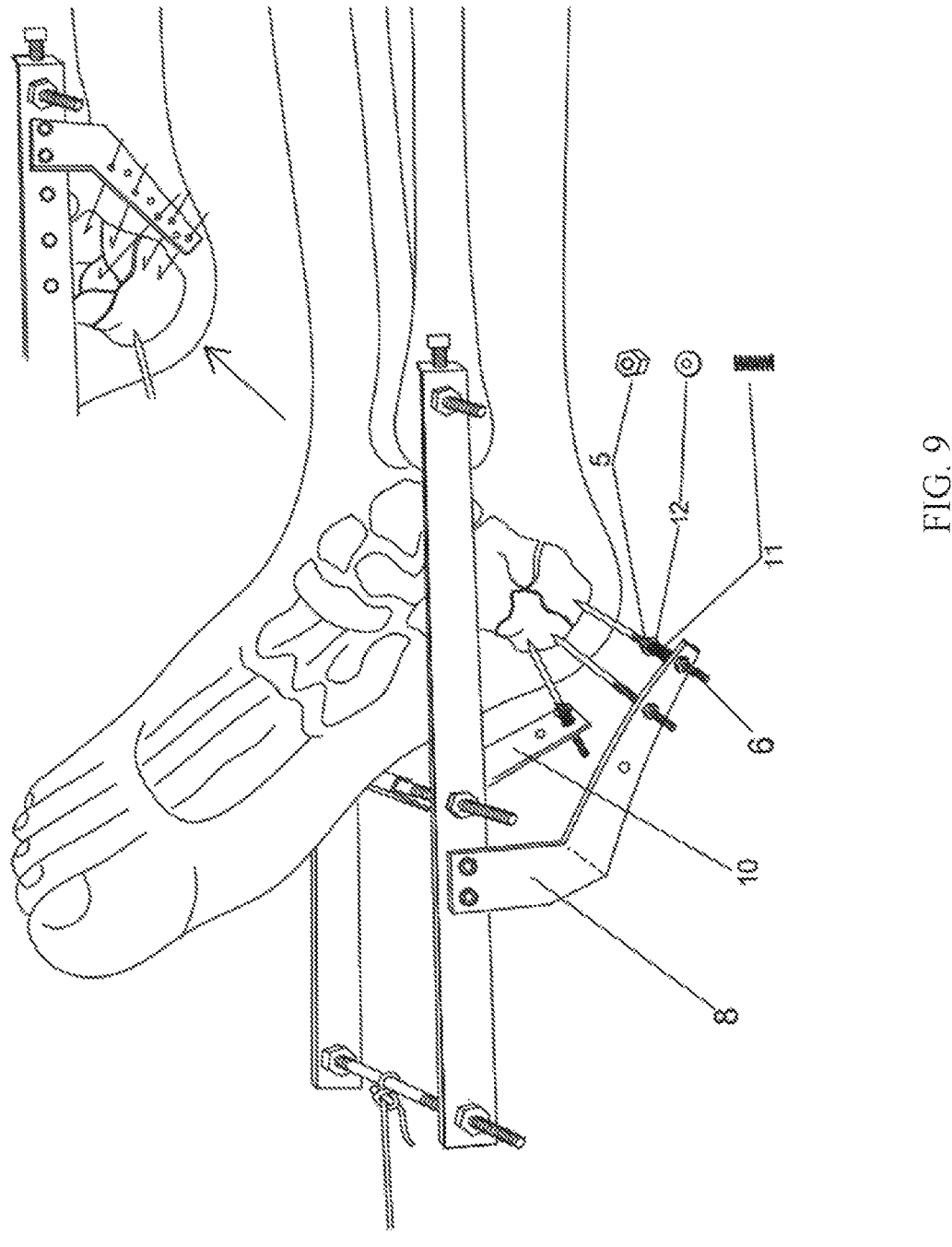

FIG. 9 is a schematic view of taking the multifunctional traction and bone fixation device to perform traction and fixation treatment to treat the heel bone having various fractures according to an embodiment of the present disclosure.

Figure 10:
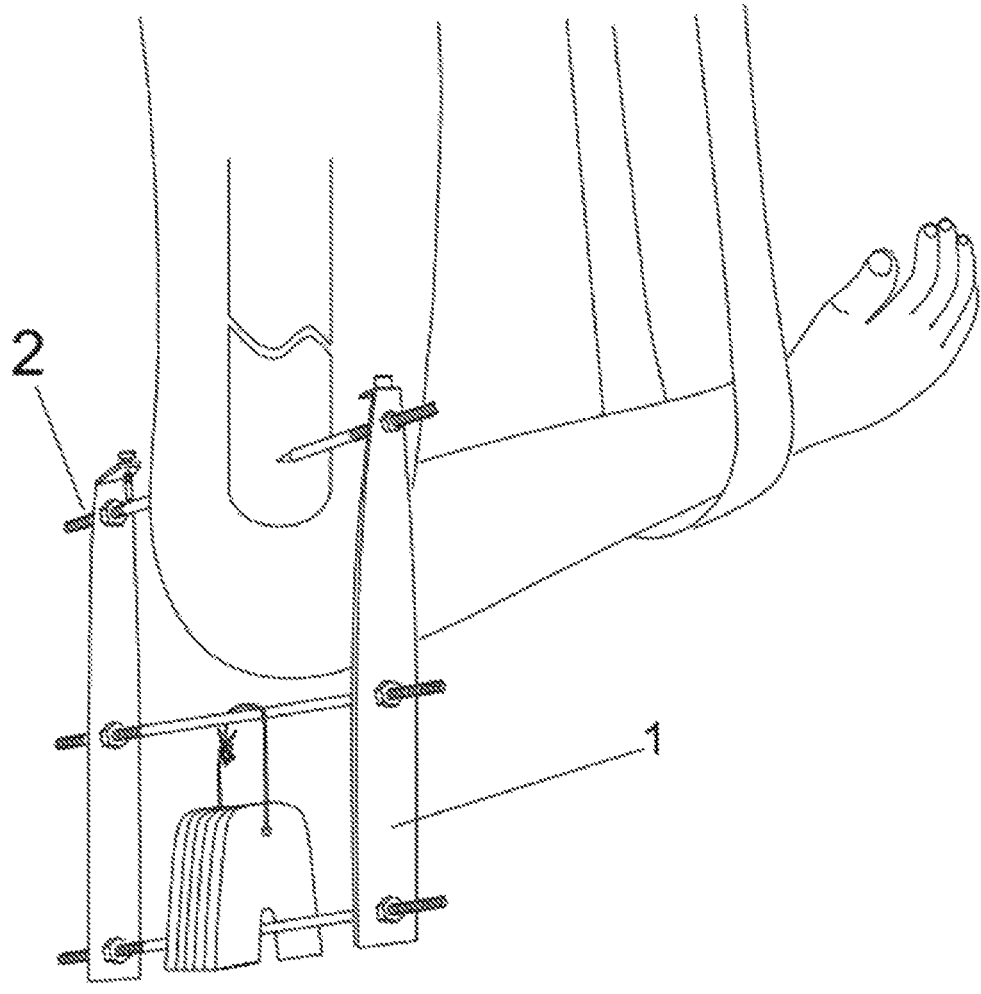

FIG. 10 is a schematic view of taking the multifunctional traction and bone fixation device to perform traction treatment to treat the fractured upper limb according to an embodiment of the present disclosure.

Figure 11:
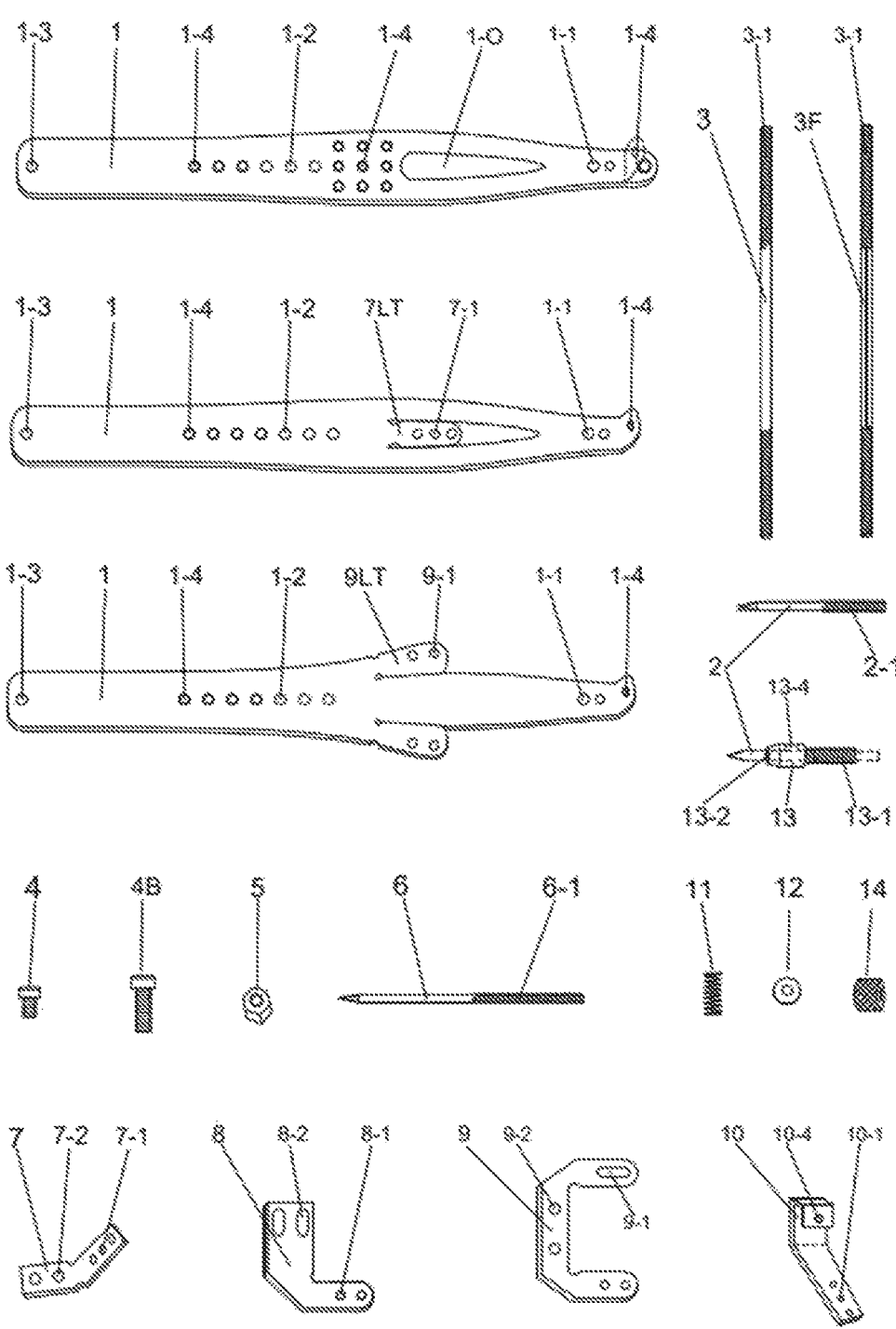

FIG. 11 shows basic components of the multifunctional traction and bone fixation device according to an embodiment of the present disclosure.

Figure 12:
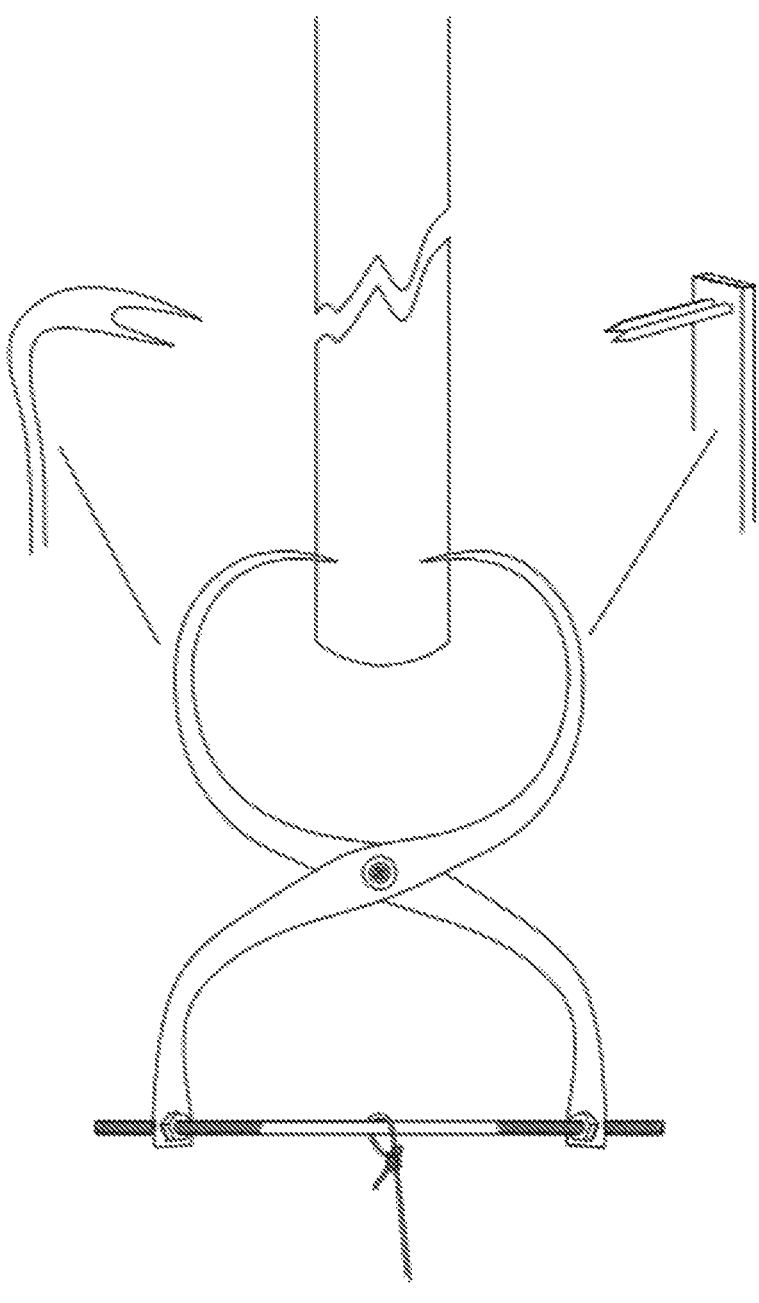

FIG. 12 is a "pincer hook" of the multifunctional traction and bone fixation device according to an embodiment of the present disclosure.

Reference numerals in the drawings: 1, traction clamping plate, (1-1) traction nail mounting hole, (1-2) second mounting hole, (1-3) third mounting hole, (1-4) screw hole, 1-0, auxiliary fixation pin hole, 2, traction nail, (2-1) screw pattern, 3, traction handle screw, (3F), positioning and pressurizing screw, (3-1) screw pattern, 4, tightening screw, 4B, nail protection screw, 5, reinforcement nut, 6, auxiliary fixing pin, (6-1) screw pattern, 7, unidirectional auxiliary fixation pin holder, 7LT, integral unidirectional auxiliary fixation pin holder, (7-1) first threading hole, (7-2) fourth mounting hole, 8, lateral auxiliary fixation pin holder, (8-1) second threading hole, (8-2) fifth mounting hole, 9, bidirectional auxiliary fixation pin holder, 9LT, integral bidirectional auxiliary fixation pin holder, (9-1) third threading hole, (9-2) sixth mounting hole, 10, foot bottom fixation pin holder, (10-1) fourth threading hole, (10-4) second screw hole, 11, spring, 12, flat pad, 13, nail protection sleeve, (13-1) screw pattern, (13-2) threading hole, (13-4) third screw hole, 14, anti-slip nut.

DETAILED DESCRIPTION

Figure 1:
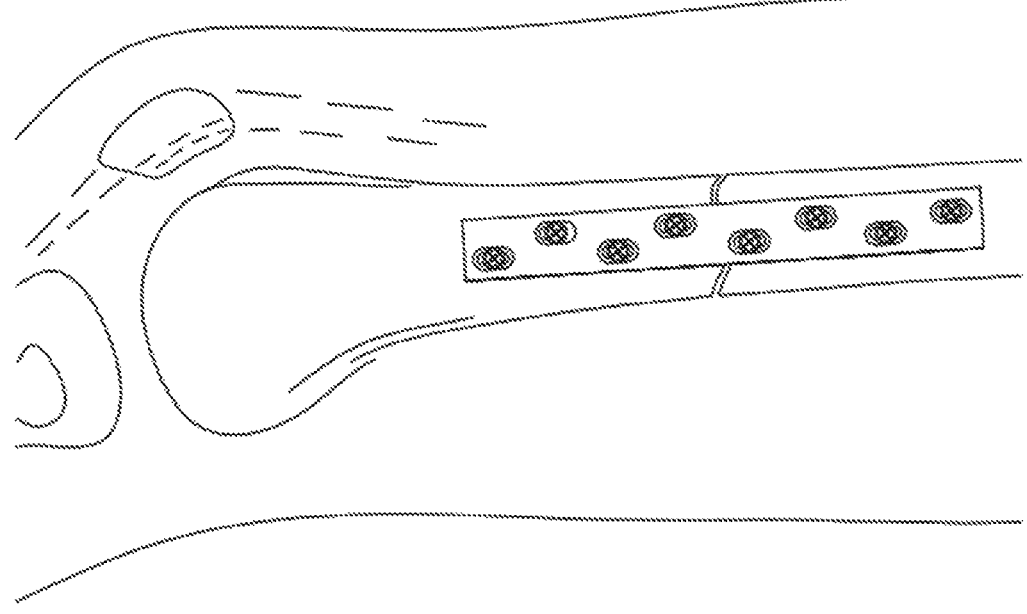
FIG. 1 is a side schematic view of taking steel plates and screws for internally fixation when preforming a traditional open surgery to treat fractures of the dice bone.

As shown in FIG. 1 and FIG. 2, when a human bone is fractured, the traditional open surgery may be performed to internally fix the fractured bone. Disadvantages of the open surgery may include the following. 1. The muscle may be cut, and a large incision may be generated. Cutting may damage tissues around the fracture of the bone. According to theoretical analysis, the human bone and the surrounding tissues are equally important. In order to connect the frac-
tured bone, the traditional open surgery may be performed to
damage the surrounding tissues, which may be comparable
to a natural disaster. When the operation is successful, the
patient may suffer from a second surgery to remove the
internal fixation. 2. Bone connection is performed under a
blurry vision due to bleeding and performed within a small
vision window which may not be observed from three sides.
The vision may be poor, and it is highly difficult to perform
the surgery. Alignment errors may occur quite often. When
the alignment error is serious, a second surgery may be
performed, even causing the patient to have lifelong dis-
ability.

FIG. 3 shows positions of the fracture site and the traction
nail, when traditional traction is performed. Disadvantages
of the traditional traction are as follows. 1. Since one nail is
configured for the traditional traction. To perform the trac-
tion, the nail may penetrate the bone. However, the human
calf includes two bones, and therefore, penetrating one nail
through the bone may not be applicable. The doctor has to
inject the traction nail into the heel bone. The heel bone and
the calf double bones do not extend in a vertical line, a
traction effect cannot be guaranteed. 2. In addition, the
traditional traction nail penetrates through the human bone,
causing vibration, and the vibration may cause the fractured
bone to be completely displaced, such that a secondary
injury may be generated. Therefore, when performing the
western treatment, the doctor may perform the open surgery
to take the steel plate for internal fixation.

As shown in FIG. 6, a multifunctional traction and bone
fixation device includes a traction clamping plate 1, a
traction nail 2, a traction handle screw 3, a positioning and
pressurizing screw 3F, a nail protection screw 4B, a rein-
forcement nut 5, a nail protection sleeve 13, an anti-slip nut
14. The traction clamping plate 1 includes a total of two
elongated plates. A front end of a body of each traction
clamping plate 1 defines a traction nail mounting hole 1-1.
A middle portion of the body of each traction clamping plate
1 defines a second mounting hole 1-2 and a screw hole 1-4.
A rear end of the body of each traction clamping plate 1
defines a third mounting hole 1-3. Atop of each traction
clamping plate 1 is bent for 90 degrees and defines the screw
hole 1-4. Alternatively, each traction clamping plate 1 is
straight. A nail protection sleeve 13 is arranged inside the
traction nail mounting hole 1-1 at the front end. The anti-slip
nut 14 or other nuts are arranged on a screw pattern 13-1 of
the nail protection sleeve and are arranged on the outside of
each of the two traction clamping plates 1 for fixation. The
second mounting hole 1-2 defined in the middle portion of
the two traction clamping plates 1 are connected to each
other by a positioning and pressurizing screw 3F. A rein-
forcement nut 5 is arranged on each of the positioning and
pressurizing screw 3F and a screw pattern 3-1 of each of two
heads of the traction handle screw 3. The reinforcement nut
5 is arranged at each of an inside and an outside of the
traction and clamping plate 1 for adjustment and fixation.
The traction nail 2 is straight and has a round cross section.
A front end of the traction nail 2 is sharp, and a rear end is
smooth and straight or is arranged with a screw pattern 2-1.
The traction nail 2 is connected to the traction clamping
plate 1 through the traction nail mounting hole 1-1. The
reinforcement nut 5 is arranged on the screw pattern 2-1 of
the traction nail 2 and is arranged at each of the inside and
the outside of each traction and clamping plate 1 for adjust-
ment and fixation. A nail protection screw 4B is arranged
inside each screw hole 1-4, which are disposed at the top of
the two traction clamping plates 1. Alternatively, the traction nail 2 is arranged inside a threading hole 13-2 of the nail
protection sleeve 13. A tightening screw 4 is arranged inside
the third screw hole 13-4. Heads of traction nails 2, which
are arranged at the front end of the two traction clamping
plates 1, are injected in opposite directions into a lower
portion of the fracture site to determine a fixation position.
The rear ends of the two traction clamping plates 1 extend
along the thigh direction to be weighted-pulled through the
traction handle screw 3.

As shown in FIG. 7, FIG. 8, FIG. 9, and FIG. 10, the
multifunctional traction and bone fixation device includes
the traction clamping plate 1, the traction nail 2, the traction
handle screw 3, the positioning and pressurizing screw 3F,
the nail protection screw 4B, the reinforcement nut 5, an
auxiliary fixation pin hole 1-0, a unidirectional auxiliary
fixation pin holder 7, a lateral auxiliary fixation pin holder
8, a bidirectional auxiliary fixation pin holder 9, a foot
bottom fixation pin holder 10, and an auxiliary fixation pin
6. The traction clamping plate 1 includes a total of two
elongated plates. The front end of a body of each traction
clamping plate 1 defines a plurality of traction nail mounting
holes 1-1. The middle portion of the body of each traction
clamping plate 1 defines a plurality of second mounting
holes 1-2 and a plurality of screw holes 1-4. The rear end of
the body of each traction clamping plate 1 defines a third
mounting hole 1-3. The top of each traction clamping plate
1 is bent for 90 degrees and defines the screw hole 1-4. The
second mounting holes 1-2 defined in the middle portion of
the two traction clamping plates 1 are connected to each
other by the positioning and pressurizing screw 3F. The third
mounting holes 1-3 defined in the rear end of the two
traction clamping plates 1 are connected to each other by the
handle screw 3. A reinforcement nut 5 is arranged on each
of the positioning and pressurizing screw 3F and a screw
pattern s 3-1 of each of two heads of the traction handle
screw 3. The reinforcement nut 5 is arranged at each of an
inside and an outside of the traction and clamping plate 1 for
adjustment and fixation. The traction nail 2 is straight and
has a round cross section. A front end of the traction nail 2
is sharp, and a rear end is smooth and straight or is arranged
with a screw pattern 2-1. The traction nail 2 is connected to
the traction clamping plate 1 through the traction nail
mounting hole 1-1. The reinforcement nut 5 is arranged on
the screw pattern 2-1 of the traction nail 2 and is arranged
at each of the inside and the outside of each traction and
clamping plate 1 for adjustment and fixation. A nail protec-
tion screw 4B is arranged inside each screw hole 1-4, which
are disposed at the top of the two traction clamping plates 1.
Heads of traction nails 2, which are arranged at the front end
of the two traction clamping plates 1, are injected in opposite
directions into a lower portion of the fracture site to deter-
mine a fixation position. The rear ends of the two traction
clamping plates 1 extend along the thigh direction by the
traction handle screw 3 to perform pulling and traction. The
auxiliary fixation pin hole 1-0 is bin-opening-shaped. A front
end of the auxiliary fixation pin hole 1-0 is disposed near the
traction nail 2, and a rear end of the auxiliary fixation pin
hole 1-0 is disposed near the unidirectional auxiliary fixation
pin holder 7. The unidirectional auxiliary fixation pin holder
7 is bent to be I-shaped. A front end of the unidirectional
auxiliary fixation pin holder 7 defines a first threading hole
7-1. A rear end of the unidirectional auxiliary fixation pin
holder 7 defines two fourth mounting holes 7-2. The unidi-
rectional auxiliary fixation pin holder 7 is connected to the
traction clamping plate 1 through the fourth mounting holes
7-2. A tightening screw 4 is arranged inside the screw hole
1-4. The fixation pin 6 is arranged inside the first threading hole 7-1. The reinforcement nut 5 is arranged on a screw pattern 6-1 of the fixation pin 6 and is arranged on each of two sides of the auxiliary fixation pin holder 7-1 for adjustment and fixation. The lateral auxiliary fixation pin holder 8 is L-shaped and has a bent side. A front end of the lateral auxiliary fixation pin holder 8 defines a second threading hole 8-1. A rear end of the lateral auxiliary fixation pin holder 8 defines two fifth mounting holes 8-2. The lateral auxiliary fixation pin holder 8 is connected to the traction clamping plate 1 through the fifth mounting holes 8-2. The tightening screw 4 is arranged inside the screw hole 1-4. The fixation pin 6 is arranged inside the second threading hole 8-1. The reinforcement nut 5 is arranged on the screw pattern 6-1 of the fixation pin 6 and is arranged on each of two sides of the auxiliary fixation pin hole 8-1 for adjustment and fixation. The bidirectional auxiliary fixation pin holder 9 is U shaped and has two sides bent. A front end of each of the two sides defines a third threading hole 9-1. A rear end of the bidirectional auxiliary fixation pin holder 9 defines two sixth mounting holes 9-2. The bidirectional auxiliary fixation pin holder 9 is connected to the traction clamping plate 1 through the sixth mounting holes 9-2. The tightening screw 4 is arranged inside the screw hole 1-4. The fixation pin 6 is arranged in the third threading hole on the two sides. The reinforcement nut 5 is arranged on the screw pattern 6-1 of the fixation pin 6 and is arranged on each of two sides of the auxiliary fixation pin holder 9 for adjustment and fixation. The integral unidirectional auxiliary fixation pin holder 7LT is disposed at a middle-front of the traction clamping plate 1. A front end of the integral unidirectional auxiliary fixation pin holder 7LT defines a threading hole 7-1, and a rear end of the integral unidirectional auxiliary fixation pin holder 7LT is connected to a bottom of the auxiliary fixation pin threading hole 1-0. When the auxiliary fixation is used, a plier may pucker the integral unidirectional auxiliary fixation pin holder 7LT and adjust the integral unidirectional auxiliary fixation pin holder 7LT to reach a determined angle. The fixation pin 6 is arranged inside the first threading hole 7-1. The reinforcement nut 5 is arranged on the screw pattern 6-1 of the fixation pin 6 and is arranged on each of two sides of the auxiliary fixation pin holder 7-1 for adjustment and fixation. The integral bidirectional auxiliary fixation pin base 9LT is disposed at two sides of the middle-front of the traction clamping plate 1. A front end of the integral bidirectional auxiliary fixation pin holder 9LT defines a threading hole 9-1, a rear end of the integral bidirectional auxiliary fixation pin holder 9LT is connected to the body of the traction clamping plate 1. When the auxiliary fixation is used, a plier may pucker the integral bidirectional auxiliary fixation pin holder 9LT and adjust the integral bidirectional auxiliary fixation pin holder 9LT to reach a determined angle. The fixation pin 6 is arranged in the third threading hole 9-1 disposed at the two sides. The reinforcement nut 5 is arranged on the screw pattern 6-1 of the fixation pin 6 and is arranged on each of two sides of the auxiliary fixation pin holder 9-1 for adjustment and fixation. The foot bottom auxiliary fixation pin holder 10 is disposed at a middle-rear portion of the traction clamping plate 1. The positioning and pressurizing screw 3F is arranged as a base. A front end of the foot bottom auxiliary fixation pin holder 10 defines a threading hole 10-1. A rear end of the foot bottom auxiliary fixation pin holder 10 defines a slot, and the slot is arranged with a screw hole 10-4. The foot bottom auxiliary fixation pin holder 10 is connected to the positioning and pressurizing screw 3F through the slot. The foot bottom auxiliary fixation pin holder 10 is displaced on the positioning and pressurizing screw 3F to reach the fixation position. The tightening screw 4 is arranged inside the second screw hole 10-4. The fixation pin 6 is arranged inside the fourth threading hole 10-1. The reinforcement nut 5 is arranged on the screw pattern 6-1 of the fixation pin 6 and is arranged on each of two sides of the foot bottom auxiliary fixation pin holder 10 for adjustment and fixation. Alternatively, a spring 11 and a flat pad 12 are disposed between the fourth threading hole 10-1 and reinforcement nut 5.

As shown in FIG. 6, a model A of the present application is provided. A method of using the multifunctional traction and bone fixation device to tract and connect bones according to a first embodiment includes following operations. 1) A patient is lying on a bed. 2) An open surgery is not performed. (After swelling is reduced) Firstly, the multifunctional traction and bone fixation device is placed properly according to displacement of fractured bones shown in an X-ray image and the width and the length of the leg. A position of the traction nail 2 is determined, and a position of the second mounting hole 1-2 in the middle portion of the traction clamping plate 1 is determined, and the fixation device is assembled (traction nail 2 may be an exception). 2) Sterilization is performed firstly. 3). Anesthetic is injected locally. 4). The doctor may successively inject two traction nails 2 in opposite directions to penetrate the cortex to be inserted into the bone about 10 mm. It may be preferable to take a special tool to press the two nails into the bone at the same time. 5). The reinforcement nut 5 is arranged on the screw pattern 2-1 of the traction nail 2, and a position of the reinforcement nut 5 is determined. 6). A side of the fixation device is loosened, and a mounting hole 1-1 of the traction clamping plate is selected to sleeve the screw pattern 2-1 of the traction nail 2. Similar operations may be performed on the other clamping plate. At the same time, the reinforcement nut 5 is arranged on the screw pattern 2-1 of the traction nail 2 at each of two sides and is fastened and fixed at the inside and the outside of each traction clamping plate 1. 7). The nail screw 4B is arranged inside screw hole 1-4 at the top of the traction clamping plate 1 is screwed tightly to abut against the traction nail 2 to protect the angle of the traction nail 2. Finally, the patient's thigh may be protected on a traction frame, and a traction weight is hung on the traction handle screw 3 to perform pulling and traction.

As shown in FIG. 7, FIG. 8, FIG. 9, and FIG. 10, models B, C, D, and H of the present disclosure are provided. A method of using the multifunctional traction and bone fixation device to tract and connect bones according to a second embodiment includes following operations. 1) The patient is lying on the bed. The patient's thigh may be protected on a traction frame. The doctor assembles the traction and bone fixation device and the auxiliary fixation pin holder and adjusts an angle of the device, based on displacement of the fractured bones shown in the X-ray image. Further, the traction nail 2 is assembled. 2) When fixing, a side of the traction clamping plate 1 is loosened, and the traction device is placed at a traction position of the leg. The traction nails 2 at the front ends of the two traction clamping plates are successively injected (it may be preferable to use a dedicated tool to inject the two nails into the bone simultaneously) in opposite directions into the bone. When it is determined that the traction nails 2 are properly injected into the bone, all reinforcement nuts 5 are screwed tightly at the same time. 3) The nail protection screw 4B is mounted into the screw hole 1-4 at the top of the traction clamping plate 1, and is tightened to abut against the traction nail 2 to protect the angle of the traction nail. Finally, the traction weight is hung on the traction handle screw 3 to perform pulling and traction. 4) After the above traction process is completed, the auxiliary fixation is assembled. 1) Firstly, a head of the auxiliary fixation pin 6 is sleeved into the threading hole, and a reinforcement nut 5 is assembled on the screw pattern 6-1 of the auxiliary fixation pin 6 from the direction of the pin head (alternatively, the spring and the flat pad may be assembled firstly, and the reinforcement 5 may be assembled subsequently). 2) The head of the auxiliary fixation pin 6 is injected into a fixation target, penetrating the cortex to abut against the displaced bone. Further, another reinforcement nut 5 is arranged at the outside of the treading hole and on the screw pattern 6-1 at the rear end of the auxiliary fixation pin. Subsequently, two reinforcement nuts 5 disposed on two sides of the auxiliary fixation are tightened simultaneously. NOTE: 1. When the spring (11) and the flat pad (12) are arranged, the reinforcement nut 5 arranged at the rear end of the fixation pin 6 may be loosened. At the same time, the reinforcement nut 5 arranged below the spring may be tightened to increase compression of the spring. 2. The above procedures of assembling the auxiliary fixation may include auxiliary fixations, such as 7, 8, 9, 10, and so on. Same assembling procedures will not be repeated, and if allowed, it may be preferable to perform the procedures under the X-ray. 3. If the leg is swelling, the auxiliary fixation target may not be determined clearly, traction may be performed for several days, and the auxiliary fixation may be performed at some days later when the leg is not swelling.

What is claimed is:

1. A multifunctional traction and bone fixation device, comprising:
two traction clamping plates,
a traction nail,
a positioning and pressurizing screw,
a traction handle screw,
a tightening screw,
a nail protection screw,
a nail protection sleeve, and
an anti-slip nut;
wherein a front end of a body of each traction clamping plate defines a traction nail mounting hole, a middle portion of the body of each traction clamping plate defines a second mounting hole and a plurality of screw holes, a rear end of the body of each traction clamping plate defines a third mounting hole; a top of each traction clamping plate is bent for 90 degrees and defines a top screw hole;
the nail protection sleeve is arranged inside the traction nail mounting hole at the front end, the anti-slip nut or another nut is arranged on a screw pattern of the nail protection sleeve and is arranged on the outside of each traction clamping plate for fixation; the second mounting hole defined in the middle portion of one of the two traction clamping plates is connected to the second mounting hole defined in the middle portion of the other one of the two traction clamping plates by the positioning and pressurizing screw,
the third mounting hole defined in the rear end of the one of the two traction clamping plates is connected to the third mounting hole defined in the rear end of the other one of the two traction clamping plates by the traction handle screw, a reinforcement nut is arranged on a screw pattern of each of two heads of the positioning and pressurizing screw and each of two heads of the traction handle screw, further, the reinforcement nut is arranged at each of an inside and an outside of each traction clamping plate for adjustment and fixation;

10 the traction nail is connected to each traction clamping plate through the traction nail mounting hole, the nail protection screw is arranged inside the top screw hole of each traction clamping plate, or the traction nail is arranged inside a threading hole of the nail protection sleeve, the tightening screw is arranged inside a third screw hole; and
a head of the traction nail, which is arranged at the front end of one of the two traction clamping plates, and a head of the traction nail, which is arranged at the front end of the other one of the two traction clamping plates, are injected in opposite directions into a lower portion of a fractured site to determine a fixation position, and the rear end of each traction clamping plate extend along a thigh direction to be weighted-pulled through the traction handle screw.

2. The multifunctional traction and bone fixation device according to claim 1, wherein the traction nail is straight and has a round cross section; a front end of the traction nail is sharp; and a rear end of the traction nail is smooth and straight or is arranged with a screw pattern;
two or more traction nails are connected and are respectively connected to the two traction clamping plates through traction nail mounting holes;
the reinforcement nut is arranged on a screw pattern of each traction nail and is arranged at each of the inside and the outside of each traction and clamping plate for adjustment and fixation, and welding or conjoining is performed to form a two-phase pincer hook.

3. A multifunctional traction and bone fixation device, comprising:
two traction clamping plates,
a traction nail,
a positioning and pressurizing screw,
a traction handle screw,
a nail protection screw,
an auxiliary fixation pin hole,
a unidirectional auxiliary fixation pin holder,
an integral unidirectional auxiliary fixation pin holder,
a lateral auxiliary fixation pin holder,
a bidirectional auxiliary fixation pin holder,
an integral bidirectional auxiliary fixation pin holder,
a foot bottom fixation pin holder, and
an auxiliary fixation pin;
wherein a front end of a body of each traction clamping plate defines a plurality of traction nail mounting holes, a middle portion of the body of each traction clamping plate defines a plurality of second mounting holes and a plurality of screw holes, a rear end of the body of each traction clamping plate defines a third mounting hole, a top of each traction clamping plate is bent for 90 degrees and defines a top screw hole, one of the plurality of second mounting holes defined in the middle portion of one of the two traction clamping plates is connected to one of the plurality of second mounting holes defined in the middle portion of an other one of the two traction clamping plates by the positioning and pressurizing screw,
the third mounting hole defined in the rear end of the one of the two traction clamping plates is connected to the third mounting hole defined in the rear end of the other one of the two traction clamping plates by the traction handle screw, a reinforcement nut is arranged on a screw pattern of each of two heads of the positioning and pressurizing screw and each of two heads of the traction handle screw, the reinforcement nut is arranged at each of an inside and an outside of one of the two traction clamping plate for adjustment and fixation;

the traction nail is connected to each traction clamping plate through the plurality of traction nail mounting holes, the reinforcement nut is arranged on a screw pattern of the traction nail and is arranged at each of an inside and an outside of each traction clamping plate for adjustment and fixation;

the nail protection screw is arranged inside the top screw hole, a head of the traction nail, which is arranged at a front end of one of the two traction clamping plates, and a head of the traction nail, which is arranged at a front end of the other one of the two traction clamping plates, are injected in opposite directions into a lower portion of a fractured site to determine a fixation position, the rear end of each traction clamping plate extend along a thigh direction to be weighted-pulled through the traction handle screw;

the middle portion of the body of each traction clamping plate is arranged with the unidirectional auxiliary fixation pin holder and the integral unidirectional auxiliary fixation pin holder, a fixation pin is arranged inside a first threading hole defined in each of a front end of the unidirectional auxiliary fixation pin holder and a front end of the integral unidirectional auxiliary fixation pin holder, the fixation pin disposed at a middle-front portion of each traction clamping plate abuts against a fractured bone to achieve auxiliary fixation;

the lateral auxiliary fixation pin holder is disposed at a middle-rear portion of each traction clamping plate, the fixation pin is arranged inside a second threading hole defined in a front end of the lateral auxiliary fixation pin holder, a head of the lateral auxiliary fixation pin disposed at the middle-rear portion of each traction clamping plate abuts against a fractured bone to achieve auxiliary fixation;

the bidirectional auxiliary fixation pin holder and the integral bidirectional auxiliary fixation pin holder are arranged on each of two sides of the middle-front portion of each traction clamping plate, the fixation pin is arranged inside a third threading hole defined in each of a front end of the bidirectional auxiliary fixation pin holder and a front end of the integral bidirectional auxiliary fixation pin holder, a head of the traction nail, which is arranged at the front end of one of the two traction clamping plates, and heads of fixation pins, which are arranged at two sides of the middle-front portion of each traction clamping plate, abut against two sites of the fractured bone to achieve auxiliary fixation.

4. The multifunctional traction and bone fixation device according to claim 3, wherein the auxiliary fixation pin hole is defined at the middle-front portion of each traction clamping plate and is bin-opening-shaped, a front end of the auxiliary fixation pin hole is disposed near the traction nail, and a rear end of the auxiliary fixation pin hole is disposed near the unidirectional auxiliary fixation pin holder.

5. The multifunctional traction and bone fixation device according to claim 3, wherein the unidirectional auxiliary fixation pin holder is bent to be I-shaped, the front end of the unidirectional auxiliary fixation pin holder defines the first threading hole, a rear end of the unidirectional auxiliary fixation pin holder defines two fourth mounting holes, the unidirectional auxiliary fixation pin holder is connected to each traction clamping plate through the fourth mounting holes, a tightening screw is arranged inside one of the plurality of screw holes, the fixation pin is arranged inside the first threading hole, the reinforcement nut is arranged on a screw pattern of the fixation pin and is arranged on each of two sides of the auxiliary fixation pin hole for adjustment and fixation.

6. The multifunctional traction and bone fixation device according to claim 3, wherein the lateral auxiliary fixation pin holder is L-shaped and has a bent side, a front end of the lateral auxiliary fixation pin holder defines a second threading hole, rear end of the lateral auxiliary fixation pin holder defines two fifth mounting holes, the lateral auxiliary fixation pin holder is connected to each traction clamping plate through the fifth mounting holes, a tightening screw is arranged inside one of the plurality of screw holes, the fixation pin is arranged inside the second threading hole, and the reinforcement nut is arranged on a screw pattern of the fixation pin and is arranged on each of two sides of the auxiliary fixation pin hole for adjustment and fixation.

7. The multifunctional traction and bone fixation device according to claim 3, wherein the bidirectional auxiliary fixation pin holder is U shaped and has two sides bent, a front end of each of the two sides defines a third threading hole, a rear end of the bidirectional auxiliary fixation pin holder defines two sixth mounting holes, the bidirectional auxiliary fixation pin holder is connected to each traction clamping plate through the sixth mounting holes, a tightening screw is arranged inside one of the plurality of screw holes, the fixation pin is arranged in the third threading hole defined in each of the two sides, the reinforcement nut is arranged on a screw pattern of the fixation pin and is arranged on each of two sides of the auxiliary fixation pin holder for adjustment and fixation.

8. The multifunctional traction and bone fixation device according to claim 3, wherein the integral unidirectional auxiliary fixation pin holder is disposed at the middle-front portion of each traction clamping plate, the front end of the integral unidirectional auxiliary fixation pin holder defines the threading hole, and a rear end of the integral unidirectional auxiliary fixation pin holder is connected to a bottom of the auxiliary fixation pin threading hole;

when the auxiliary fixation is applied, a plier is configured to pucker the integral unidirectional auxiliary fixation pin holder and adjust the integral unidirectional auxiliary fixation pin holder to reach a determined angle, the fixation pin is arranged inside the first threading hole, the reinforcement nut is arranged on a screw pattern of the fixation pin and is arranged on each of two sides of the auxiliary fixation pin hole for adjustment and fixation.

9. The multifunctional traction and bone fixation device according to claim 3, wherein the integral bidirectional auxiliary fixation pin base is disposed at each of two sides of the middle-front portion of each traction clamping plate, the front end of the integral bidirectional auxiliary fixation pin holder defines the threading holes, a rear end of the integral bidirectional auxiliary fixation pin holder is connected to the body of each traction clamping plate;

when the auxiliary fixation is applied, a plier is configured to pucker the integral bidirectional auxiliary fixation pin holder and adjust the integral bidirectional auxiliary fixation pin holder to reach a determined angle, the fixation pin is arranged in one of the third threading holes, the reinforcement nut is arranged on a screw pattern of the fixation pin and is arranged on each of two sides of the auxiliary fixation pin holder for adjustment and fixation.

10. The multifunctional traction and bone fixation device according to claim 3, wherein the foot bottom auxiliary fixation pin holder is disposed at the middle-rear portion of
each traction clamping plate, the positioning and pressuriz-
ing screw is configured to be a base, a front end of the foot
bottom auxiliary fixation pin holder defines a threading hole,
a rear end of the foot bottom auxiliary fixation pin holder
defines a slot, the slot is arranged with a second screw hole,
the foot bottom auxiliary fixation pin holder is connected to
the positioning and pressurizing screw through the slot, the
foot bottom auxiliary fixation pin holder is displaced on the
positioning and pressurizing screw to reach the fixation
position, the tightening screw is arranged inside the second
screw hole, the fixation pin is arranged inside the fourth
threading hole, the reinforcement nut is arranged on a screw
pattern of the fixation pin and is arranged on each of two
sides of the foot bottom auxiliary fixation pin holder for
adjustment and fixation; or a spring and a flat pad are
disposed between the fourth threading hole and reinforce-
ment nut.

* * * * *

14